(12) United States Patent
Lamphere et al.

(10) Patent No.: US 6,251,291 B1
(45) Date of Patent: Jun. 26, 2001

(54) RESERVOIR-AND-FILTER SYSTEM AND METHOD OF USE

(75) Inventors: David G. Lamphere, Framingham; Thomas D. Headley, Wellesley; Clair L. Strohl, Norfolk; Clifford Martin, Medway, all of MA (US)

(73) Assignee: Tranfusion Technologies Corporation, Natick, MA (US)

( * ) Notice: Subject to any disclaimer, the term of this patent is extended or adjusted under 35 U.S.C. 154(b) by 0 days.

(21) Appl. No.: 09/221,089

(22) Filed: Dec. 28, 1998

(51) Int. Cl.⁷ .................................................. B01D 35/02
(52) U.S. Cl. .................... 210/767; 210/314; 210/316; 210/434; 210/436; 604/406; 55/318
(58) Field of Search .................................. 210/188, 232, 210/295, 299, 314–317, 436, 456, 472, 248, 335, 433.1, 434, 767; 604/4, 5, 403, 406, 4.01, 5.01; 422/44; 55/318

(56) References Cited

U.S. PATENT DOCUMENTS

| | | | |
|---|---|---|---|
| 3,768,653 | 10/1973 | Brumfield | 210/188 |
| 4,054,523 | 10/1977 | Ingenito et al. | 210/188 |
| 4,115,277 | 9/1978 | Swank | 210/436 |
| 4,243,531 | * 1/1981 | Crockett et al. | 210/436 |
| 4,531,954 | 7/1985 | Klein | 55/159 |
| 4,561,868 | 12/1985 | von Reis et al. | 55/319 |
| 4,673,423 | 6/1987 | Yumlu | 55/319 |
| 4,704,203 | 11/1987 | Reed | 210/188 |
| 4,743,371 | 5/1988 | Servas et al. | 210/188 |
| 4,758,337 | 7/1988 | Köhn et al. | 210/94 |
| 4,898,572 | 2/1990 | Lasnier et al. | 604/4.01 |
| 4,954,251 | 9/1990 | Barnes et al. | 210/806 |
| 5,015,388 | 5/1991 | Pusineri et al. | 210/641 |
| 5,055,198 | 10/1991 | Shettigar | 210/650 |
| 5,133,703 | 7/1992 | Boehringer et al. | 604/317 |
| 5,183,569 | 2/1993 | Kyriacou | 210/636 |
| 5,215,519 | 6/1993 | Shettigar | 604/4.01 |
| 5,223,154 | 6/1993 | MacPherson, Jr. et al. | 210/790 |
| 5,411,705 | * 5/1995 | Thor et al. | 210/436 |
| 5,674,173 | 10/1997 | Hlavinka et al. | 494/17 |
| 5,770,073 | * 6/1998 | Bach et al. | 210/436 |
| 5,800,721 | * 9/1998 | McBride | 210/436 |
| 5,879,624 | * 3/1999 | Boehringer et al. | 210/645 |

FOREIGN PATENT DOCUMENTS 0 771 570 A1   7/1997   (EP) .

* cited by examiner

Primary Examiner—Joseph W. Drodge
(74) Attorney, Agent, or Firm—Bromberg & Sunstein LLP

(57) ABSTRACT

A reservoir-and filter system for receiving fluid and for removing impurities from fluid is provided in an embodiment of the invention. The system includes a housing with at least two cavities; a first cavity with at least one unfiltered-fluid inlet and a second cavity with at least one filtrate outlet. In this embodiment, a filter member is disposed so as to separate the cavities. In addition, a filtering trap is disposed so as to directly accept fluid as it enters the first cavity, filter it, and minimize clogging of the filter member. A coarse filter shroud providing a funnel shape at the opening of a cup-shaped trap is included in a preferred embodiment. In an embodiment, at least one gas outlet adaptable for connection to a vacuum source is associated with the second cavity. A method for removing impurities from blood within an extracorporeal circuit is also provided in a further embodiment.

19 Claims, 9 Drawing Sheets

RESERVOIR-AND-FILTER SYSTEM AND METHOD OF USE

TECHNICAL FIELD

This invention generally relates to systems for receiving, storing, and filtering fluids in preparation for further filtrate processing. More particularly, the invention relates to the processing of blood or other biological fluids.

BACKGROUND ART

A noteworthy application of reservoir-and-filter systems is use in blood and other biological fluid processing. For example, suctioning of blood away from surgical sites may be a high throughput operation if much fluid is quickly generated.

Many state-of-the-art reservoir-and-filter systems are designed having an essentially planar filter disposed so as to divide the reservoir into separated portions. A first portion is intended for containing unfiltered fluid derived from a source while the other portion holds filtrate. Common practice is to orient the filter so that the portions are laterally adjacent to one another with the filter surface situated perpendicular to the force of gravity. Fluid is urged into the reservoir by applying a partial vacuum and passes through the planar filter after enough fluid has been collected in the resevoir to create sufficient head pressure to force the fluid through the filter. Necessarily, such a filter will clog during high throughput usage as there are limited or no safe mechanisms for detaching impurities from the filter during operation. Clogging normally occurs, due to gravity, at the lowest portion of the filter and, with time, reduces the effective operational filtration area and traps a volume of unfiltered fluid. Gradually, the filter will tend to clog at higher and higher levels and trap greater volumes of unfiltered fluid. The ability to efficiently filter the fluid will, with time, be compromised.

SUMMARY OF THE INVENTION

In a first embodiment of the invention, there is provided a reservoir-and-filter system for receiving fluid and for removing impurities from the fluid. The embodiment includes a housing which has at least two cavities. Further, the housing has at least one unfiltered-fluid inlet in fluid communication with the first cavity, and has at least one filtrate outlet in fluid communication with the second cavity. A filter member, is disposed within the housing so as to separate the first cavity from the second cavity. The filter member retains a portion of the impurities while permitting impeded fluid communication between the first and second cavities. In accordance with this embodiment, a filtering trap is also included. The trap may be cup shaped, having an opening, a bottom and sides defining a chamber. Such a filter cup has its opening disposed within the first cavity proximal to the inlet and oriented so as to accept fluid into the chamber and to collect the impurities at the bottom while permitting fluid communication through the sides between the chamber and the first cavity. Further, the depth of a filter cup measures less than the height of the first cavity permitting overflow of fluid from the chamber into the first cavity. Another embodiment further includes a coarse filter shroud disposed so as to provide a funnel shape at the trap opening. The second cavity may, in a preferred embodiment, further include at least one gas outlet adaptable for connection with a source of vacuum.

The reservoir-and-filter system may be used in a range of potential applications. A particular embodiment provides for its use as part of an extracorporeal blood processing apparatus. During certain surgical procedures, it is desirable to expeditiously remove generated blood and by-products from the surgical site. The system facilitates the collection of unfiltered blood. Unwanted blood impurities, residue and clots are then filtered, and the resulting filtrate may be further processed. An embodiment of the system provides that the housing is made from a transparent material which is compatible with blood.

In accordance with another embodiment of the invention, a method for removing impurities from blood within an extracorporeal circuit includes placing a reservoir-and-filter system in the circuit between an unfiltered blood source and a location maintained at lowered pressure, introducing blood to the circuit, and collecting filtrate. The reservoir-and-filter system includes a housing, a filter member, and a filtering trap with features described above.

DETAILED DESCRIPTION OF SPECIFIC EMBODIMENTS

Various embodiments of the reservoir-and-filter system described herein address a number of shortcomings inherent in previous designs. For example, premature clogging of single filter systems results in reduced filtrate throughput. This clogging causes diminished effectiveness of a partial vacuum or other differential pressurization mechanisms in urging the unfiltered fluid from its source and in urging the filtrate to its destination.

Figure 1:
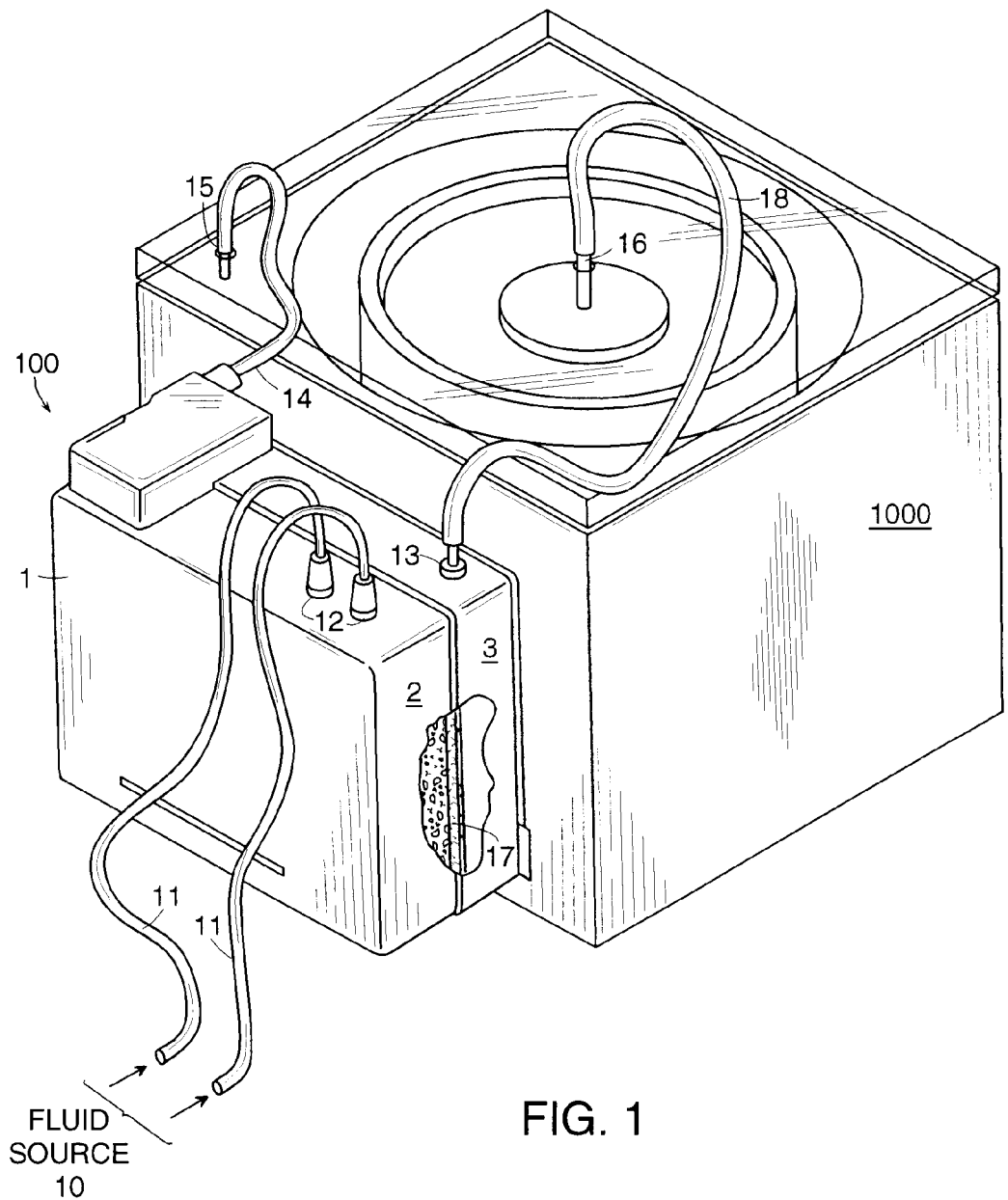
FIG. 1 is an isometric view of a reservoir-and-filter system, in accordance with an embodiment of the invention, illustrating linkages with other components, such as a blood processing device, in fluid communication with the system.

FIG. 1 illustrates linkages with other components which may be in fluid communication with a reservoir-and-filter system 100, the system according to an embodiment of the invention. System 100 is shown connected to a blood processing device 1000 as an example of how system 100 may be used in an extracorporeal blood circuit. Unfiltered fluid obtained from a fluid source 10 is directed into a reservoir 1 through unfiltered-fluid inlets 12. In a specific application, the fluid source 10 may be in communication with a surgical site where blood, debris, and other fluids are generated. During a surgical procedure, it may be critical that blood, as well as other fluids and debris, be expeditiously removed from the surgical site as quickly as such products evolve. The velocity and amount of blood generated is dependent upon the particular surgical procedure. System 100 is designed to efficiently collect and filter fluid from a range of throughput procedures. A vacuum source 15 is connected to the reservoir 1 by vacuum line 14. The illustration shows a situation in which the vacuum may be useful to the blood processing device 1000 as well as for urging fluid through system 100. A differential pressure is established causing fluid flow from the fluid source 10 into the reservoir 1. The blood processing device 1000 may employ a partial vacuum to draw filtrate from the system's filtrate outlet 13 and into the inlet 16 of a centrifuge rotor. In this embodiment, the reservoir 1 is divided into an inlet cavity 2 and an adjacent outlet cavity 3. A filter member 17 is shown disposed so as to physically separate inlet cavity 2 from outlet cavity 3. Filter member 17 may have one or may have a plurality of filtering layers. In accordance with a preferred embodiment, filter member 17 has at least one foam layer and a mesh screen. The mesh screen may be disposed adjacent to outlet cavity 3. The foam layers do not clog as quickly as does mesh screen; foam layers allow fluid to pass around physical obstacles (such as debris or impurities) as opposed to a mesh screen which, if clogged, leads to subsequently ineffective filtering and throughput of fluid.

Fluid is first drawn, using differential pressurization techniques (such as creation of a partial vacuum) from the fluid source 10, through input lines 11 and unfiltered-fluid inlets 12 into inlet cavity 2. As the volume of fluid (and as a result, fluid height) increases in inlet cavity 2, head pressure will build, until a breakthrough pressure is reached, at which point, fluid is urged through filter member 17 leaving debris behind, with filtrate entering outlet cavity 3. Filtrate may then exit outlet cavity 3 through filtrate outlet 13 and be further processed by, in this embodiment, device 1000. Partial vacuum or other differential pressurization (in a preferred embodiment, generated by or associated with device 1000) is used to draw filtrate from outlet cavity 3. Output line 18 directs fluid into the centrifuge inlet 16 of device 1000 which separates the various fluid components for future use.

Figure 2:
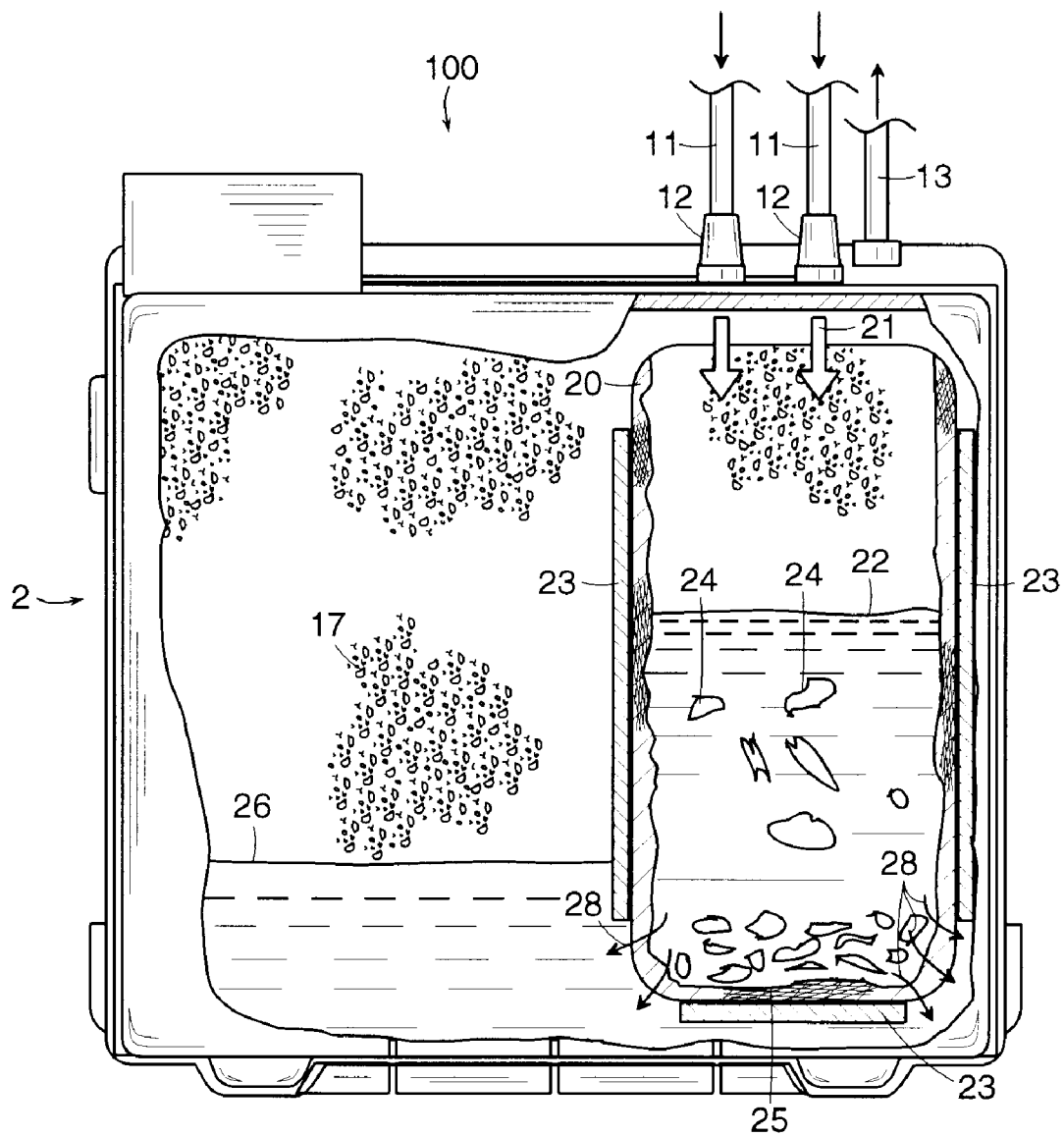
FIG. 2 is a side view of a first cavity of a reservoir-and-filter system according to an embodiment of the invention.

FIG. 2 is a side view of the inlet cavity 2 of a reservoir-and-filter system 100 according to a preferred embodiment of the invention. Unfiltered fluid is urged through inlets 12 directly into a filtering trap 20 disposed within the inlet cavity 2. In this embodiment, the filtering trap has a cup shape. Arrows 21 indicate the fluid flow direction. The filter cup 20 is oriented to accept the incoming unfiltered fluid into its chamber unless and until the chamber overflows. The chamber fluid level 22 is shown for a condition of a partially filled filter cup 20. The filter cup 20 is supported, as schematically represented by cup supports 23, so that it is held in position despite applied vacuum to the reservoir 1 while receiving and filtering fluid. Not shown are beneficial structural supports which not only may be connected with cup supports 23 but may be strategically placed within inlet cavity 2 (and outlet cavity 3 to buttress the entire reservoir 1 from collapse due to the vacuum applied during operation. Debris 24 remains in the filter cup 20, settling at or near a cup bottom 25. Thus, the chamber of the filter cup 20, while clogging with debris 24 near the cup bottom 25, is capable of filtering fluid and permitting filtrate to flow through the sides of the cup 20 into the rest of the inlet cavity 2. Filtering arrows 28 illustrate filtrate flow direction out of the filter cup 20. Inlet cavity fluid level 26 is shown. In a normal flow condition (no cup overflow), no debris 24 is available to undesirably clog the filter member 17 (shown schematically). However, in an overflow condition, some fluid will flow directly from inlets 12 into the inlet cavity 2 without passing through the filter cup 20. In this condition, some debris 24 would reach the filter member 17 and serve to undesirably clog the filter member 17. The overflow condition is designed to only occur when the rate of incoming unfiltered fluid exceeds the rate of filtering performed by the filter cup 20 or when the filter cup 20 is filled with debris. In this condition, the system 100 will perform similarly to performance of single filter systems of the prior art. Filtering trap 20 may be made from foam material chosen based upon the rate of required filtering for a given procedure. The foam material may be similar in nature to that used as a filtering layer of filter member 17. As with prior art systems, any unfiltered fluid within the rest of inlet cavity 2 will be filtered by filter member 17 allowing only filtrate to flow into outlet cavity 3. However, according to an embodiment of the present invention, with system 100, most of the fluid reaching filter member 17 will already be filtrate. Filtrate will pass quickly into outlet cavity 3 and, thereafter, pass to its destination.

Figure 3:
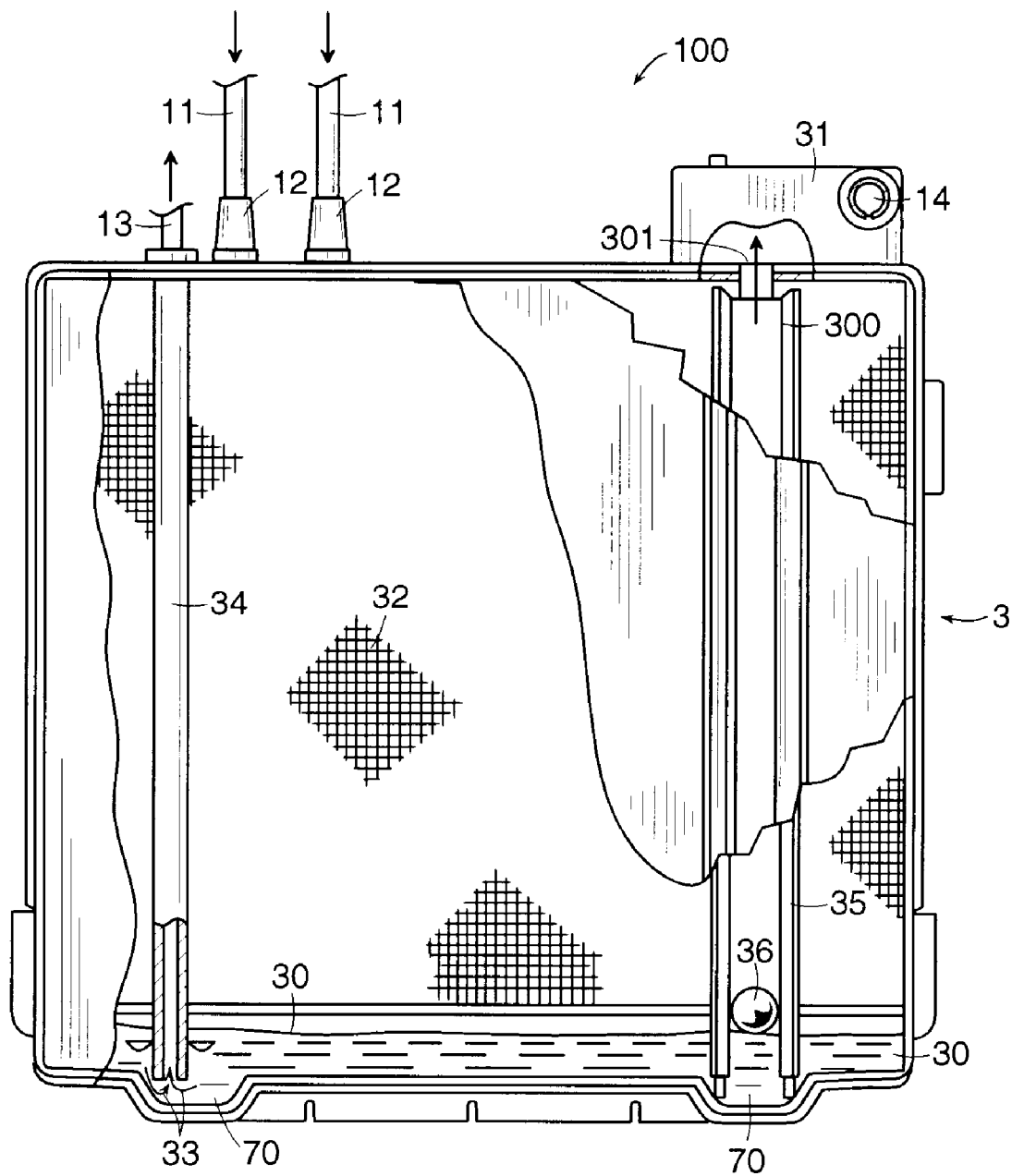
FIG. 3 is a side view of a second cavity of a reservoir-and-filter system according to an embodiment of the invention.

FIG. 3 is a side view of the outlet cavity 3 of a reservoir-and-filter system 100 according to an embodiment of the invention. Outlet cavity fluid level 30 is shown. A cutaway view of vacuum line 14 is shown coupled with cap 31. Within cap 31 there may, in a preferred embodiment, be disposed a microbial or other barrier material designed to isolate the contents of reservoir 1 from the vacuum line 14 and from the external environs. In the embodiment shown, a mesh screen 32 portion of filter member 17 (shown schematically) acts as a filtering layer and provides necessary lateral support.

In this embodiment, hollowed out areas 70 are provided in outlet cavity 3. So long as the reservoir 1 is held upright during operation, filtrate which flows through filter member 17 will first collect in areas 70. When a partial vacuum, creating a differential pressure is applied to filtrate outlet 13, filtrate will flow from an area 70 shown below tube 34, upward out of the outlet cavity 3 through tube 34 and filtrate outlet 13 in the direction of arrows 33. In accordance with the embodiment illustrated, a float tube 35 is oriented essentially vertically and positioned above a hollowed out area 70. The float tube 35 has an upper float tube end 300 disposed so as to mate with orifice 301 disposed in cap 31. A float 36 is vertically positioned within float tube 35 at or near the outlet cavity fluid level 30 due to the buoyancy of float 36. The float 36 is sized to seat within orifice 301 in the event that the outlet cavity fluid level 30 is such that the entire outlet cavity 3 is full of fluid. When the float 36 is seated within orifice 301, cap 31, and, therefore, vacuum source 15 via vacuum line 14, is removed from communication with outlet cavity 3. In such condition, the partial vacuum being created via vacuum line 14 will be blocked and additional fluid will not be urged into system 100 until level 30 decreases and float 36 is unseated from orifice 301. In a preferred embodiment, the partial vacuum used for drawing fluid out of the outlet cavity 3 to the device 1000 may be further controlled so as not to be activated if level 30 is lower than a defined threshold height.

Figure 4:
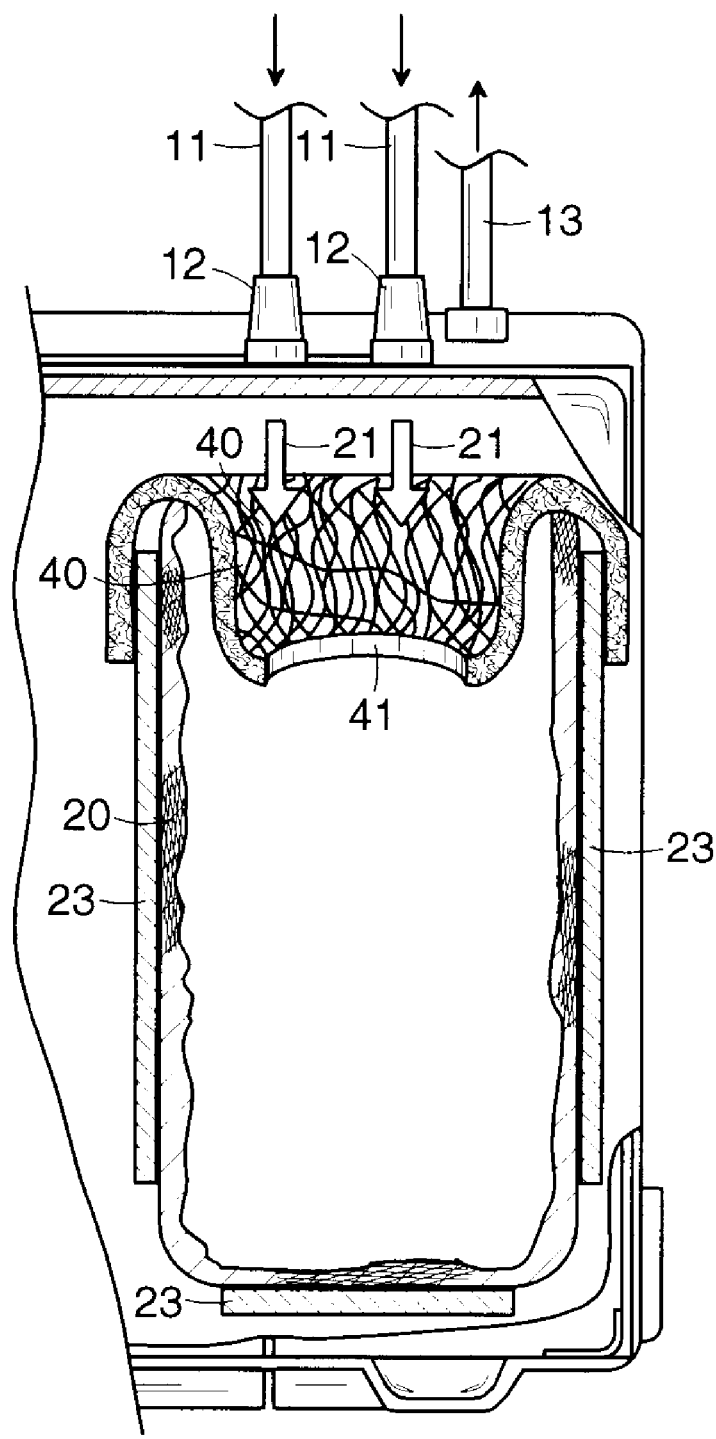
FIG. 4 is a side view of an installed filtering trap according to an embodiment of the invention.

FIG. 4 is a side view of an installed filtering trap 20 according to an embodiment of the invention. According to this preferred embodiment, a coarse filter shroud 40 is disposed so as to provide a funnel shape at the opening of filtering trap 20 (shown as having a cup shape) which receives incoming unfiltered fluid from inlets 12. The shroud 40 is made from a much more coarse filtering material than that of the filter cup 20 or of the filter member 17. The coarse filtering material should allow downward flow of unfiltered fluid and associated impurities and debris into the cup 20 both through an opening 41 cut into the shroud 40 and, to a lesser extent, from the coarse filtering material of which shroud 40 consists. The shape of the shroud 40 causes most of the unfiltered fluid to be directed first to the bottom of the filter cup 20. Since the partial vacuum tends to cause the unfiltered fluid to spray, the shroud 40 keeps the unfiltered fluid from spraying directly on the side walls of the cup 20. Additionally, some impurities and debris may be trapped by the shroud 40 as unfiltered fluid is directed into filter cup 20.

Figure 5:
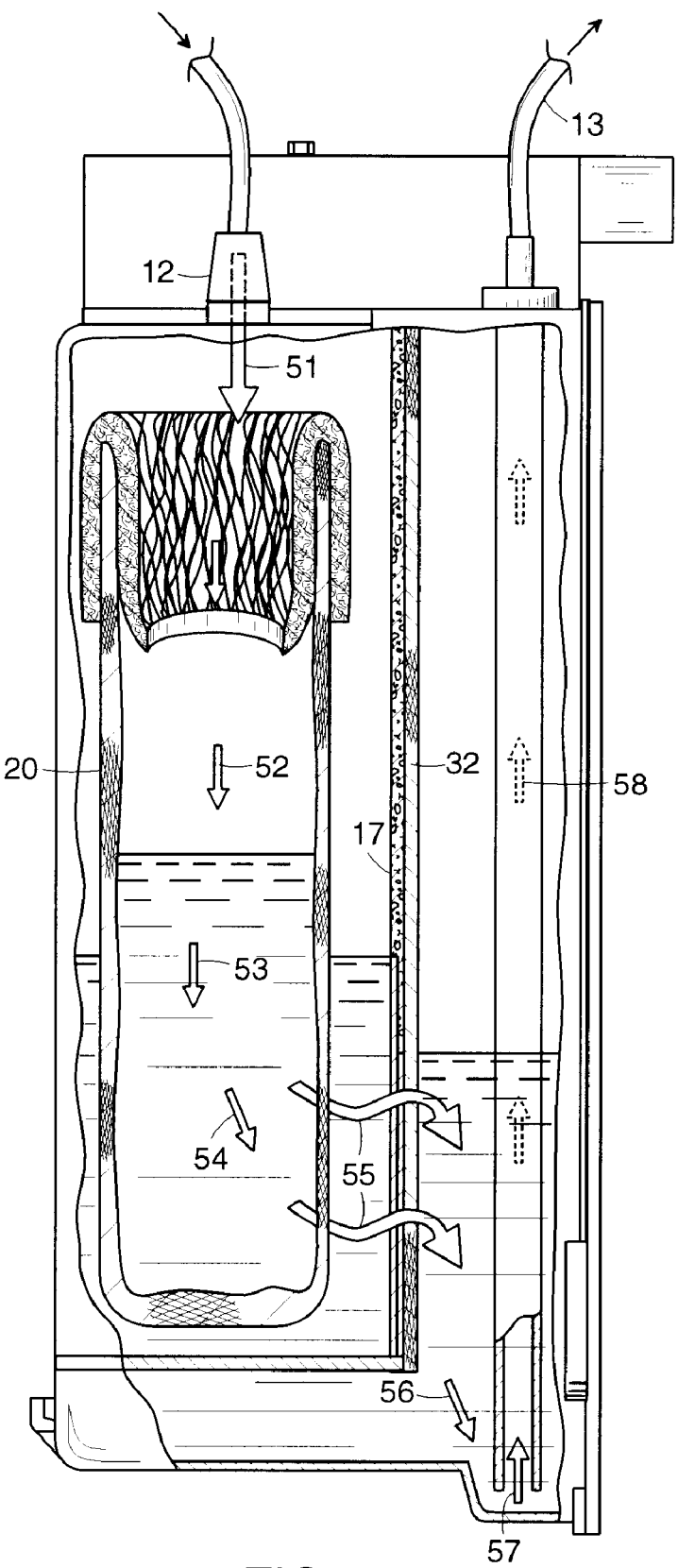
FIG. 5 is a schematic illustrating fluid flow from an inlet, into a reservoir, through a filtering trap and member, and out of the reservoir according to an embodiment of the invention.

FIG. 5 illustrates sequential fluid flow from unfiltered-fluid inlet 12, into inlet cavity 2, via directional arrow 51 into filter cup 20, sequentially in the directions of arrows 52, 53, 54, 55, 56, 57, and 58, exiting through filtrate outlet 13. Most of the fluid will be filtered by the filter cup 20 and not tend to clog filter member 17.

Figure 6:
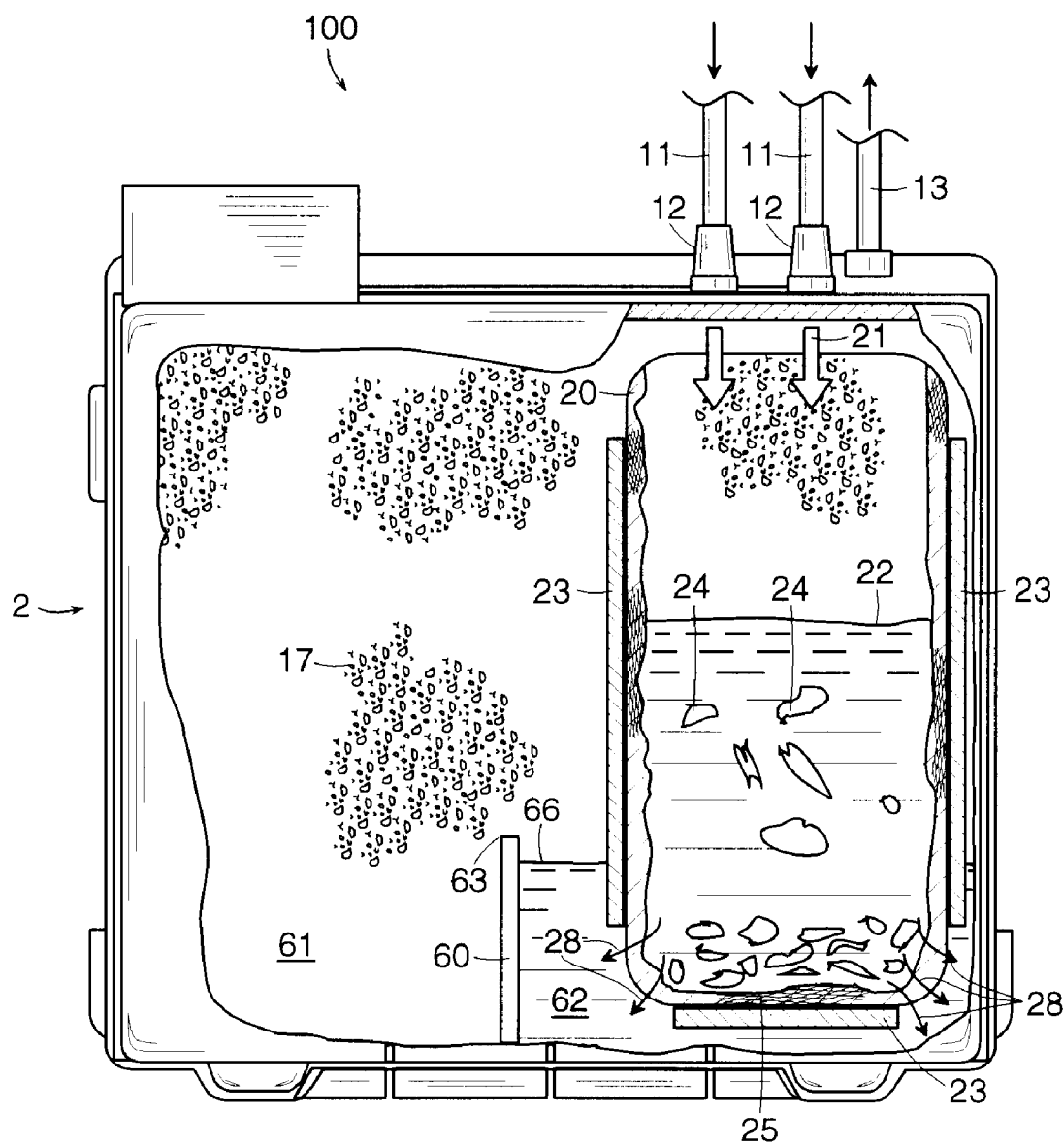
FIG. 6 is a side view of the first cavity of a reservoir-and-filter system according to another embodiment of the invention.
Figure 7:
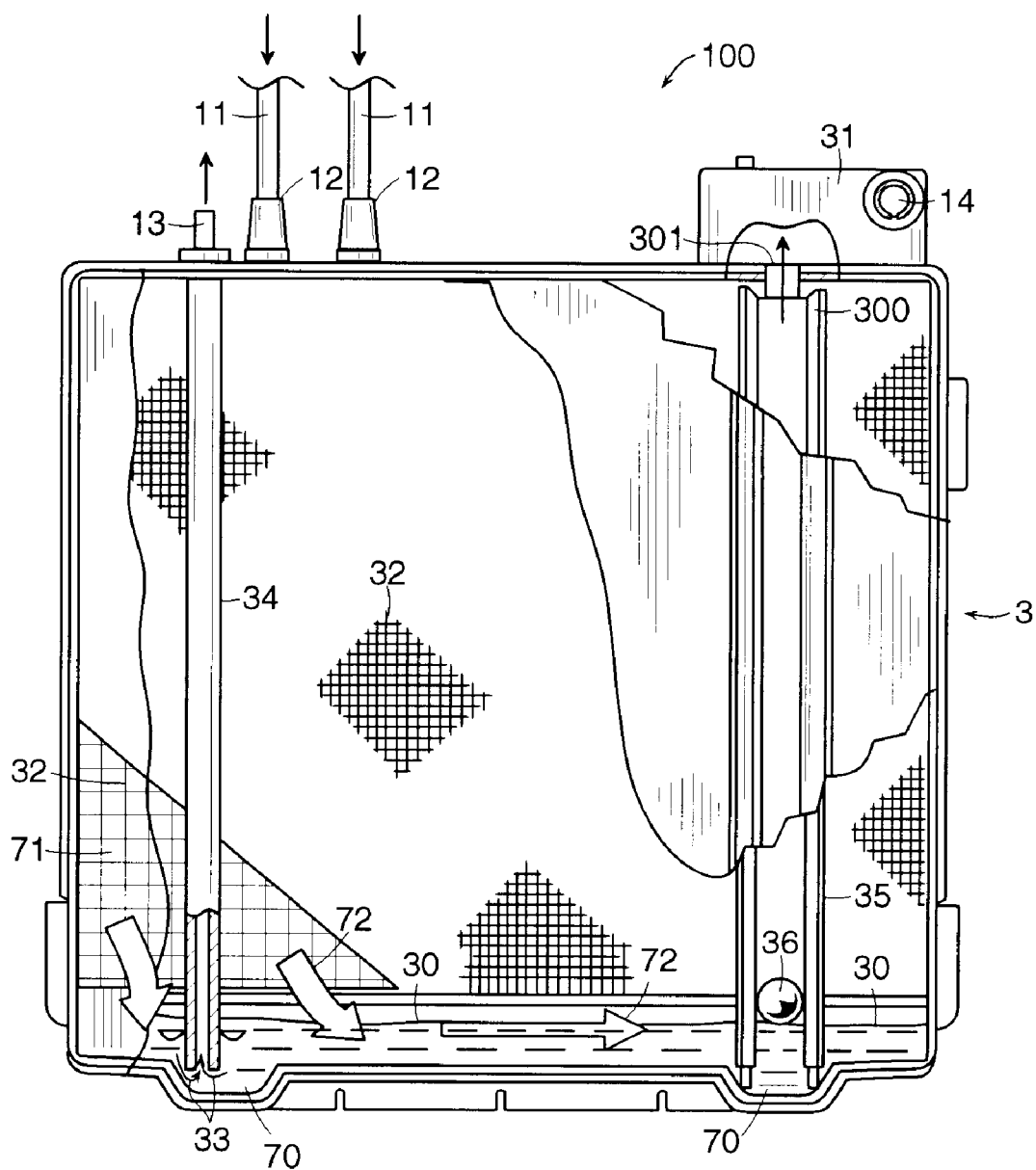
FIG. 7 is a side view of the second cavity according to the embodiment of FIG. 6.

FIG. 6 is a side view of the inlet cavity 2 of a reservoir-and-filter system 100 according to another embodiment of the invention. In this embodiment, inlet cavity 2 is divided by separator 60 into a first subcavity 61 and a second subcavity 62. Separator 60 may be made from solid material or from foam material. Foam material may be of similar quality to that used for the filtering trap 20. First subcavity 61 will not receive fluid until inlet subcavity fluid level 66 reaches and exceeds the top 63 of a solid material separator 60. If separator 60 is a foam baffle, some filtered fluid may escape to first subcavity 61 at a lower subcavity fluid level 66.) By creating subcavities, less fluid is necessary to create sufficient head pressure to break through filter member 17. In this embodiment, increased throughput of filtrate into outlet cavity 3 may be facilitated by having filter member 17 consist solely of mesh screen portion 32 (rather than having a plurality of layers) in the area adjacent to filtering trap 20. This area containing a single mesh screen 32 may be further reduced to that area disposed at a height equal to and below top 63. Structural members (not shown) incorporated to stabilize the system 100 may, alternatively, be economically used as boundaries of the area of filter member 17 having only single mesh screen. The embodiment described above is thought to speed an initial flow of filtrate to outlet cavity 3 in circumstances in which expedited "priming" of system 100 is desirable. In particular, this may be important when quicker onset of processing by an associated device 1000 is necessary. FIG. 7 illustrates how filtrate would first enter outlet cavity 3 through a triangular shaped area 71 containing a single mesh screen 32 as filter member 17. Fluid flow arrows 72 further illustrate how level 30 increases.

The reservoir-and-filter system 100 is, according to another embodiment, made from transparent material to facilitate viewing of fluid flow and fluid level. Methyl methacrylate acrylonitrile butadiene styrene (MABS) polymer is such a material which has been successfully demonstrated. Reservoir 1 is shown as generally rectangular in shape, but is in no way limited by such illustration. Structural members should be included within the inlet cavity 2 and the outlet cavity 3 for various purposes. One such purpose is to provide the required rigidity for structural stability under operational pressure. Another would be for such structural members to additionally serve as supports 23 for the filtering trap 20, the tube 34, and the filter member 17. Efficient use of such members for convenient boundaries for adjustment of the makeup of filter member 17 was previously described. The structural members may also be used to create subcavities within inlet cavity 2. The system 100 is economically designed so that it is disposable after a single application.

Figure 8:
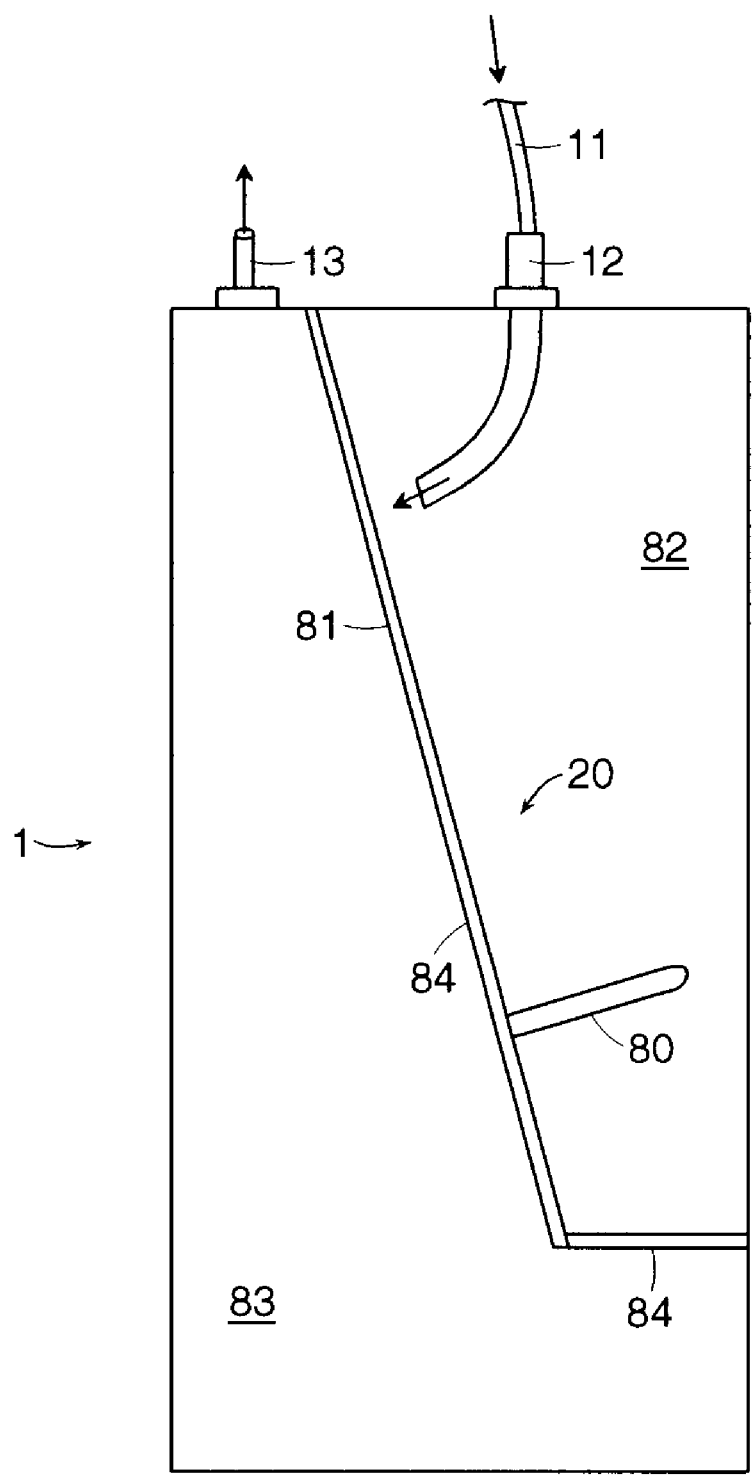
FIG. 8 is a cross-sectional view of a reservoir-and-filter system according to a further embodiment of the invention.

FIG. 8 illustrates another embodiment of the invention utilizing a generally rectangular reservoir 1. In this embodiment, inlets 12 and trap 20 are angled with respect to the reservoir 1. Trap 20 occupies a larger portion of inlet cavity 82 with debris collected at a trap side 80 rather than a "bottom" 81. The bottom 81 also acts as the filter member 84 separating inlet cavity 82 from outlet cavity 83. Trap side 80 acts as a "shelf" because of its orientation, with the remainder of inlet cavity 82 (outside trap 20) disposed below trap 20 rather than lateral to trap 20. Trap side 80 may be made from foam similar to that used in embodiments described above.

Figure 9:
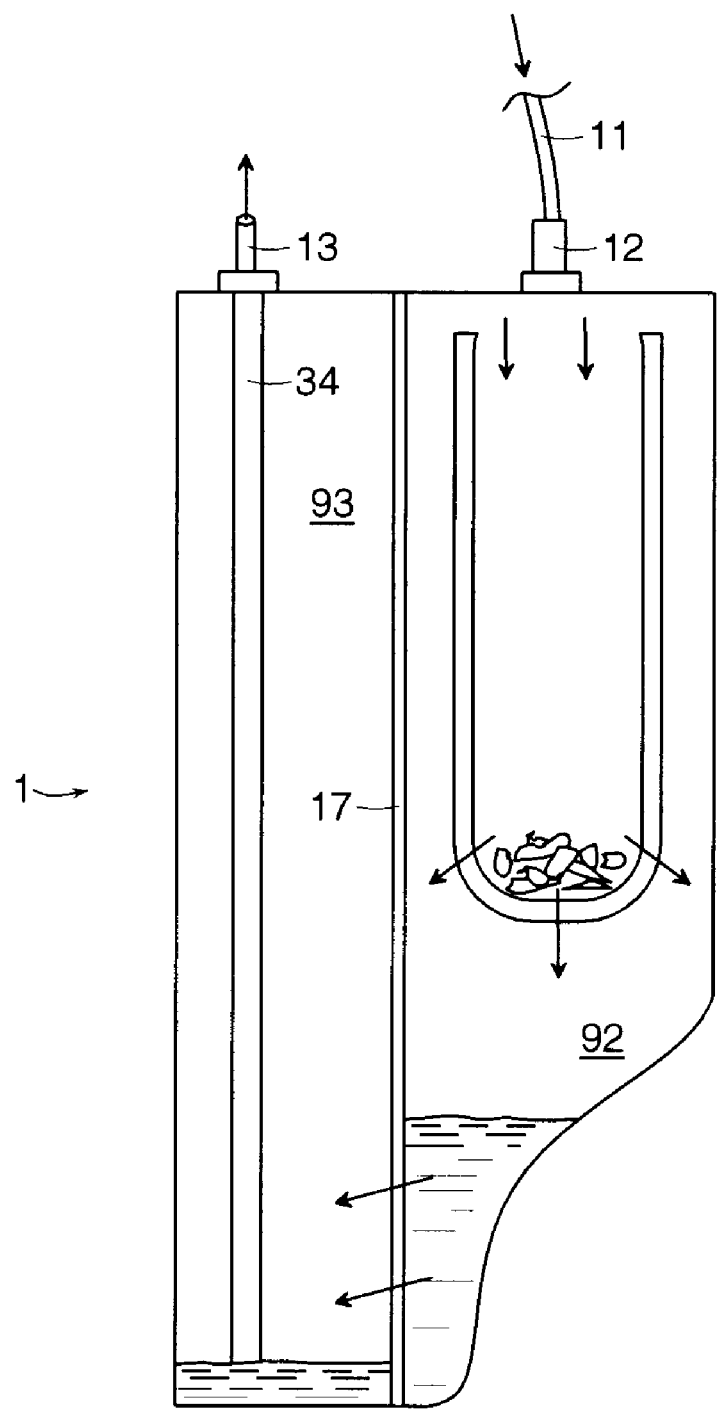
FIG. 9 is a cross-sectional view of another embodiment of a reservoir-and-filter system.

FIG. 9 illustrates yet another embodiment of the invention. Here, inlet cavity 92 is contoured so that, during the initial stages of filtering, fluid height increases more per unit of fluid volume than for the rectangular configuration described above. Increases in fluid height are proportional to the increases in pressure to urge fluid through filter member 17 to outlet cavity 93. This may be important when quicker onset of processing by an associated device 1000 is necessary.

The system 100 is suited for use in an extracorporeal blood circuit. In this application, impurities are removed from blood which originates from a surgical site. All materials used for system construction would be blood compatible per industry standards and regulations.

Blood discharged from a post-operative wound drain may also be received through an inlet (separate from inlets 12) and filtered. In such an embodiment, reservoir 1 could be further segmented to separate such unfiltered wound drain blood and resulting filtrate from that blood obtained from the surgical site.

In yet another embodiment, an appropriate light deflecting material may be used to surround the float tube 35, to provide suitable contrast for viewing the float 36. Some form of sensor known in the art may then be used to detect the position of float 36 within float tube 35 to inform as to the fluid level in the reservoir 1. Further, system 100 may be used to continue to collect blood from a post-operative wound drain as described above. A sensor, as previously noted, may also be used to monitor the amount of wound drain blood being processed. If such amount exceeds a pre-set threshold, an alarm could be included in system 100 to alert staff.

A method for removing impurities from blood within an extracorporeal circuit includes placing a system 100 in the circuit, introducing blood to the circuit, and collecting filtrate is also herein disclosed.

Although the invention has been described with reference to preferred embodiments, it will be understood by one of ordinary skill in the art that various modifications can be made without departing from the spirit and the scope of the invention, as set forth in the claims hereinbelow.

What is claimed is:

1. A reservoir-and-filter system for receiving fluid and for removing impurities from the fluid, the system comprising:
   a housing, defining a plurality of cavities, the housing having at least one unfiltered-fluid inlet in fluid communication with a first cavity, and having at least one filtrate outlet in fluid communication with a second cavity;
   a filter member disposed within the housing so as to separate the first cavity from the second cavity, wherein the member retains a portion of the impurities while permitting impeded fluid communication between the first and second cavities; and a filtering trap, the trap comprising a side and a top and defining a trap volume, the trap disposed within the first cavity proximal to the at least one unfiltered-fluid inlet and oriented so as to accept fluid, the trap permitting impeded fluid communication through the side, wherein a gap is provided around the top for permitting relatively unimpeded overflow of fluid from the trap volume into the remainder of the first cavity.

2. A reservoir-and-filter system according to claim 1, further comprising:

a coarse filter shroud, the shroud disposed so that the relatively unimpeded overflow of fluid flows from the trap volume through the shroud into the remainder of the first cavity.

3. A reservoir-and-filter system for receiving fluid and for removing impurities from the fluid the system comprising:

a housing defining first and second cavities, the housing having at least one unfiltered-fluid inlet in fluid communication with a first cavity, and having at least one filtrate outlet in fluid communication with a second cavity;

a filter member disposed within the housing so as to separate the first cavity from the second cavity, wherein the member retains a portion of the impurities while permitting impeded fluid communication between the first and second cavities; and a filter cup, having an opening, a bottom and at least one side defining a chamber, the opening disposed within the first cavity proximal to the at least one unfiltered-fluid inlet and oriented so as to accept unfiltered fluid into the chamber, the cup permitting impeded fluid communication through the at least one side, the cup being disposed so as to permit overflow of fluid from the chamber into the first cavity.

4. A reservoir-and-filter system according to claim 1, wherein the fluid is extracorporeal blood.

5. A reservoir-and-filter system according to claim 4, wherein the housing is made from a transparent material which is compatible with blood.

6. A reservoir-and-filter system according to claim 3, wherein the second cavity further includes at least one gas outlet adaptable for connection with a source of vacuum.

7. A reservoir-and-filter system according to claim 6, wherein the fluid is extracorporeal blood.

8. A reservoir-and-filter system according to claim 3, wherein the filter cup is capable of collecting the impurities at the bottom while permitting fluid communication through the at least one side between the chamber and the first cavity.

9. A reservoir-and-filter system according to claim 8, wherein the filter member includes a plurality of filtering layers disposed so that unfiltered fluid must pass through all of the layers before reaching the second cavity.

10. A reservoir-and-filter system according to claim 9, wherein one of the plurality of filtering layers is a mesh screen.

11. A reservoir-and-filter system according to claim 10, further comprising:

a separator, the separator disposed so as to partition the first cavity into two subcavities, wherein the filter cup is disposed within a first subcavity, the separator limiting fluid communication between the chamber and a second subcavity.

12. A reservoir-and-filter system according to claim 11, wherein a portion of the filter member adjacent the first subcavity is a single filtering layer.

13. A reservoir-and-filter system according to claim 12, wherein the single filtering layer is the mesh screen.

14. A reservoir-and-filter system according to claim 8, further comprising:

a separator, the separator disposed so as to partition the first cavity into two subcavities, wherein the filter cup is disposed within a first subcavity, the separator limiting fluid communication between the chamber and a second subcavity.

15. A reservoir-and-filter system for receiving fluid and for removing impurities from the fluid, the system comprising:

a housing, having a height and defining first and second cavities, the housing having at least one unfiltered-fluid inlet in fluid communication with a first cavity, and having at least one filtrate outlet in fluid communication with a second cavity;

a filter member disposed within the housing so as to separate the first cavity from the second cavity, wherein the member retains a portion of the impurities while permitting impeded fluid communication between the first and second cavities; and a filter cup, having an opening, a bottom and sides and defining a chamber having a depth, the opening disposed within the first cavity proximal to the at least one unfiltered-fluid inlet and oriented so as to accept fluid into the chamber, the depth measuring less than the height so as to permit overflow of fluid from the chamber into the first cavity; and a coarse filter shroud, the shroud disposed so as to provide a funnel shape at the opening of the filter cup.

16. A method for removing impurities from blood within an extracorporeal circuit, the method comprising:

placing a reservoir-and-filter system in the circuit between an unfiltered blood source and a location maintained at lowered pressure, the reservoir-and-filter system comprising:

a housing, defining a plurality of cavities, the housing having at least one unfiltered-fluid inlet in fluid communication with a first cavity, and having at least one filtrate outlet in fluid communication with a second cavity;

a filter member disposed within the housing so as to separate the first cavity from the second cavity, wherein the member retains a portion of the impurities while permitting impeded fluid communication between the first and second cavities; and a filtering trap, the trap comprising a side and defining a trap volume, the trap disposed within the first cavity proximal to the at least one unfiltered-fluid inlet and oriented so as to accept blood, the trap permitting impeded fluid communication through the side, wherein a gap is provided around the top for permitting relatively unimpeded overflow of blood from the trap volume into the remainder of the first cavity;

introducing blood to the circuit; and collecting filtrate from the filtrate outlet.

17. A method for removing impurities from blood within an extracorporeal circuit, the method comprising:

placing a reservoir-and-filter system in the circuit between an unfiltered-blood source and a location maintained at lowered pressure, the reservoir-and-filter system comprising:

a housing defining first and second cavities, the housing having at least one unfiltered-blood inlet in fluid communication with the first cavity and having at least one filtrate outlet in fluid communication with the second cavity;

a filter member disposed within the housing so as to separate the first cavity from the second cavity, wherein the filter member retains a portion of the impurities while permitting impeded fluid communication between the first and second cavities; and a filter cup, having an opening, a bottom and at least one side defining a chamber, the opening disposed within the first cavity proximal to the at least one unfiltered-blood inlet and oriented so as to accept blood into the chamber, the cup permitting impeded fluid communication through the at least one side, the cup being disposed so as to permit overflow of blood from the chamber into the first cavity;

introducing blood to the circuit; and collecting filtrate from the filtrate outlet.

18. A method according to claim 17, wherein, in placing, the filter cup is capable of collecting the impurities at the bottom while permitting impeded fluid communication through the at least one side between the chamber and the first cavity.

19. A method for removing impurities from blood within an extracorporeal circuit, the method comprising:

placing a reservoir-and-filter system in the circuit between an unfiltered blood source and a location maintained at lowered pressure, the reservoir-and-filter system comprising:

a housing, having a height and defining first and second cavities, the housing having at least one unfiltered-blood inlet in fluid communication with the first cavity and having at least one filtrate outlet in fluid communication with the second cavity;

a filter member disposed within the housing so as to separate the first cavity from the second cavity, wherein the filter member retains a portion of the impurities while permitting impeded fluid communication between the first and second cavities;

a filter cup, having an opening, a bottom and sides and defining a chamber having a depth, the opening disposed within the first cavity proximal to the at least one unfiltered-fluid inlet and oriented so as to accept fluid into the chamber, the depth measuring less than the height so as to permit overflow of blood from the chamber into the first cavity; and a coarse filter shroud, the shroud disposed so as to provide a funnel shape at the opening of the filter cup;

introducing blood to the circuit; and collecting filtrate from the filtrate outlet.

* * * * *